United States Patent [19]
Bolden

[11] Patent Number: 6,090,086
[45] Date of Patent: Jul. 18, 2000

[54] EYE DROP APPLICATOR WITH ADJUSTABLE GUIDE ARM AND IMPROVED CLOSURE SYSTEM

[76] Inventor: Amos Bolden, 1802 Hamill Rd., Apt. 12, Hixon, Tenn. 37343

[21] Appl. No.: 09/185,479

[22] Filed: Nov. 3, 1998

[51] Int. Cl.[7] .................................................. A61M 35/00
[52] U.S. Cl. ........................ 604/302; 604/300; 604/295
[58] Field of Search ..................................... 604/294, 295, 604/300, 301, 302; 215/306; 222/419, 420, 421

[56] References Cited

U.S. PATENT DOCUMENTS

| | | | |
|---|---|---|---|
| 3,860,135 | 1/1975 | Yung et al. | 215/213 |
| 4,054,221 | 10/1977 | Glover | 215/235 |
| 4,543,096 | 9/1985 | Keene | 604/300 |
| 4,605,398 | 8/1986 | Herrick | 604/300 |
| 4,789,082 | 12/1988 | Sampson | 222/1 |
| 4,915,268 | 4/1990 | Lay et al. | 222/498 |
| 4,973,322 | 11/1990 | Jewart | 604/300 |
| 5,007,905 | 4/1991 | Bauer . | |
| 5,030,214 | 7/1991 | Spector . | |
| 5,064,420 | 11/1991 | Clarke et al. . | |
| 5,133,702 | 7/1992 | Py . | |
| 5,207,657 | 5/1993 | Gibilisco | 604/295 |
| 5,267,986 | 12/1993 | Py . | |
| 5,366,448 | 11/1994 | Basilice et al. . | |
| 5,387,202 | 2/1995 | Baron . | |
| 5,398,837 | 3/1995 | Degrassi | 220/337 |
| 5,578,019 | 11/1996 | Feldman . | |
| 5,578,020 | 11/1996 | Mosley . | |
| 5,611,788 | 3/1997 | Marchment . | |
| 5,618,274 | 4/1997 | Rosenthal . | |
| 5,665,079 | 9/1997 | Stahl . | |
| 5,795,342 | 8/1998 | Shapiro et al. | 604/300 |
| 5,848,999 | 12/1998 | Basilice et al. | 604/300 |

*Primary Examiner*—Mark O. Polutta
*Assistant Examiner*—David J. Cho
*Attorney, Agent, or Firm*—Pitts & Brittian, P.C.

[57] ABSTRACT

An eye drop applicator which has an adjustable guide arm. The guide arm defines a semi-rigid member attached to an eye drop container. The guide arm serves as a point of tactile reference to the user who seeks to dispense liquid eye medicament. It further serves as a retractor of the lower eyelid, thereby allowing the user to place eye drops accurately and efficiently into the conjunctiva. The eye drop applicator can be manipulated with one hand, and avoids the necessity of the user placing his or her fingers near the eye socket, thereby maximizing the sterility and effectiveness of the medicament. Moreover, its configuration can be adjusted so as to conform to the shape of the user's face. The eye drop applicator also presents an improved closure system. A cap is placed over the nozzle of an eye drop container to seal the contents. Access to the eye drops is obtained by opening a cover at the end of the cap. Removing the cover exposes an opening in the cap through which eye drops are dispensed. In order to maintain sterility of the cover and the opening in the cap, and to insure ready access to the cover, the cover is tethered to the cap.

4 Claims, 6 Drawing Sheets

EYE DROP APPLICATOR WITH ADJUSTABLE GUIDE ARM AND IMPROVED CLOSURE SYSTEM

TECHNICAL FILED

This invention pertains to the field of eye drop dispensing devices. More particularly, it relates to the field of those eye drop dispensing devices which allow for the proper positioning of the dispensing device over the eye with the use of one hand so as to provide for the safe and easy application of the ocular medicament.

BACKGROUND ART

The conventional eye drop container is a small, cylindrical bottle having nozzle. Eye drops are dispensed into the eye by positioning the bottle in a mostly inverted position over the eye, and gently compressing the bottle in order to force medicative solution through the nozzle and into the eye. This procedure requires the user to first tilt his or her head back into a substantially horizontal position. The user must then retract one or both eyelids from the eye with one hand, while dispensing eye drops with the other.

For most people, the procedure for dispensing eye drops is difficult and imprecise. With the conventional dispenser, the user attempts to drop medicament directly onto the surface of the eyeball. This produces unwanted blinking and natural tear flow due to the particular sensitivity of the conjunctiva. This, in turn, limits the time in which the medicament remains effective.

The preferred area of the eye for dispensing is the lower eyelid, or conjunctival sac. Yet, the use of a conventional eye drop container makes it difficult to align the nozzle with the conjunctival sac.

An additional obstacle to the proper dispensing of eye drops is the risk of contamination to the medicament. With the conventional eye drop dispenser, the user is required to place the fingers of one hand in close proximity to the eye so as to retract the upper and/or lower eyelids from the surface of the eyeball. This creates a risk of contamination of the medicament, as well as infection of the eye.

Further, it is well known that any detachable parts of the dispenser, such as the cap, must be set aside during the application process. The cap then becomes a source of contamination when it comes into contact with dirt or other particles from the surfaces upon which it rests. The contaminant is transmitted to the dispensing device when the cap is reinstated over the nozzle.

The patent literature presents various examples of proposed solutions to overcome the difficulties described above. Typical of the art are those devices disclosed in the following U.S. Patents:

| U.S. Pat. No. | Inventor(s) | Issue Date |
| --- | --- | --- |
| 5,007,905 | Bauer | April 1991 |
| 5,030,214 | Spector | July 1991 |
| 5,064,420 | Clarke, et al. | November 1991 |
| 5,133,702 | Py | July 1992 |
| 5,267,986 | Py | December 1993 |
| 5,366,448 | Basilice, et al. | November 1994 |
| 5,387,202 | Baron | February 1995 |
| 5,578,019 | Feldman | November 1996 |

-continued

| U.S. Pat. No. | Inventor(s) | Issue Date |
| --- | --- | --- |
| 5,578,020 | Mosley | November 1996 |
| 5,611,788 | Marchment | March 1997 |
| 5,665,079 | Stahl | September 1997 |

Most of the above referenced patents (U.S. Pat. Nos. 5,007,905, 5,030,214, 5,064,420, 5,133,702, 5,264,986, 5,366,448, 5,387,202, 5,578,019, 5,611,788, and 5,665,079) disclose various eye drop dispensers which utilize a fixed eyelid retractor. These fixed retractors are mounted onto an existing bottle, and cannot be adjusted to properly fit the shape of the user's ocular region.

Another drawback to many of the above referenced patents (U.S. Pat. Nos. 5,064,420, 5,007,905, 5,133,702, and 5,366,448, 5,378,202, 5,578,020, and 5,611,788) is that the dispensing device requires virtually a 90-degree angle between the vertical axis of the bottle and the surface of the conjunctiva. This means that the liquid medicament is applied to the patient in a manner which is uncomfortable and imprecise.

Many of the dispensing devices available actually encompass the eye drop bottle itself These operate purely by tactile, rather than visual, feedback. See, e.g., U.S. Pat. Nos. 5,267, 986, 5,387,202, and 5,030,214 and 5,578,020. With these devices, neither the user nor one assisting the user can visually monitor the progress of the liquid as it is dispensed from the bottle.

Finally, a drawback to prior art is that the cap and, perhaps, the dispenser itself, is detachable. This presents a risk of contamination. U.S. Pat. No. 5,578,019 seeks to eliminate this problem by providing a pivoting cap over the nozzle to the eye drop bottle. Rotation of the cap to and away from the axis of the container serves to open and close the bottle. However, the internal surface of the pivoting closure assembly cannot be accessed for cleaning in the event it becomes dirty while in its open state. Moreover, the use of a pivoting closure assembly increases the cost of manufacture and complexity of use.

It is an object of the present invention to provide an eye drop applicator which allows for the dispensing of liquid ocular medication in such a manner that the user need not place his or her fingers near the surface of the eye.

It is also an object of the present invention to provide for an eye drop applicator whose use does not necessitate tilting of the head by the user at an uncomfortable or inconvenient angle.

It is an additional object of the present invention to provide a simple eye drop dispenser which is easy to use, i.e., which can be used with one hand while accurately instilling drops in the conjunctiva, and in such a manner that the user can visually monitor the progress of the liquid as dispensed from the bottle.

It is further an object of the invention to provide a single eye drop dispenser capable of exposing the conjunctival sac of the user regardless of the shape or configuration of their face.

Another object of the invention is to provide an eye drop dispenser having an adjustable guiding arm which secures to any conventional eye drop container, thereby creating an inexpensive means for improving eye drop containers currently available.

Finally, it is an object of the present invention to provide an eye drop dispenser which can be easily cleaned and sealed so as to facilitate sterility.

DISCLOSURE OF THE INVENTION

Other objects and advantages will be accomplished by the present invention which provides an apparatus for accurately and safely dispensing liquid ocular medication, or eye drops. In accordance with the present invention, there is provided a bottle having an adjustable guiding arm for administering liquid eye drops. Also provided is a closure system which need not be detached from the apparatus while eye drops are being dispensed.

The apparatus of the present invention first comprises a container for holding liquid eye drops. This container is flexible, allowing the user to exert delicate external force upon it so as to squeeze eye drops therefrom. At its top end, the container forms a neck such that the container is shaped like a bottle. The neck of the container extends to a tip having a port. This enables the neck to serve as a nozzle. During dispensation, eye drops are gently squeezed from the bottle and, with the aid of gravity, exit through the port in the nozzle.

Attached externally to the nozzle of the container is a guide arm. This is a semi-rigid member which extends from the container. The distal end of the guide arm is placed under the user's eye in contact with the lower eyelid or cheek. This positioning of the guide arm allows the user to retract his or her lower eyelid away from the eye socket while at the same time positioning the port of the bottle over the conjunctiva. The guide arm also provides tactile feedback for proper positioning of the bottle. In this way, liquid medicament can be safely and accurately administered.

A removable cap resides over the nozzle of the container. The bottle cap is configured to closely fit the nozzle, and to cover the port.

In the present invention, the bottle cap remains in place even during the administration of eye drops. This is accomplished by providing a removable cover at the tip of the nozzle. This cover is tethered to the cap itself so that it need not be placed on an unsterile surface during dispensation of the eye drops. Hence, the cover is attached to the cap whether it is in its open or closed position.

BRIEF DESCRIPTION OF THE DRAWINGS

The above mentioned features of the invention will become more clearly understood from the following detailed description of the invention read together with the drawings in which:

FIG. 1a presents the cover of the cap in its open position.

DESCRIPTION OF THE PREFERRED EMBODIMENT

Figure 1A:
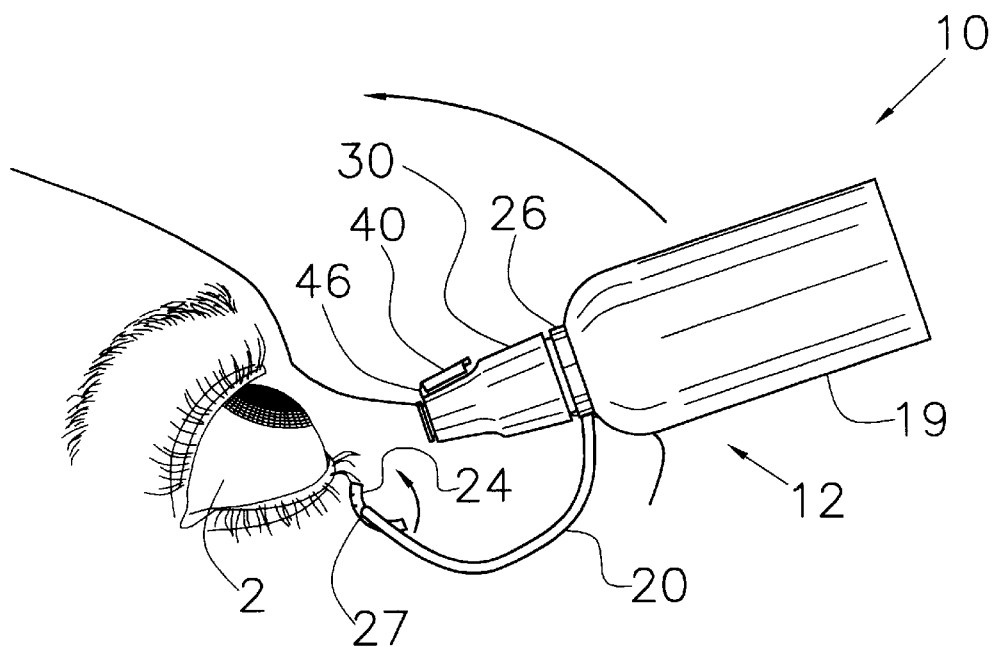
FIG. 1a is a perspective view of the eye drop applicator of the present invention being positioned near the eye of a user, with the lower eyelid of the user ready to be retracted by the guide arm. In addition.
Figure 1B:
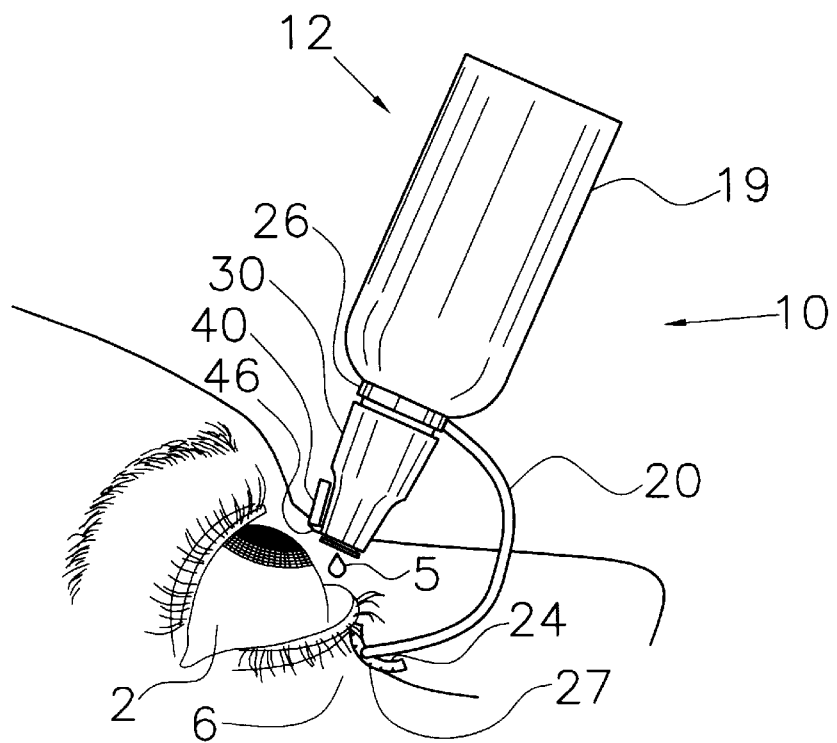
FIG. 1b is a perspective view of the eye drop applicator of FIG. 1a, with the applicator moved into position over the eye of a user so as to safely and accurately dispense medicament. At this point, the eyelid is being retracted.
Figure 2:
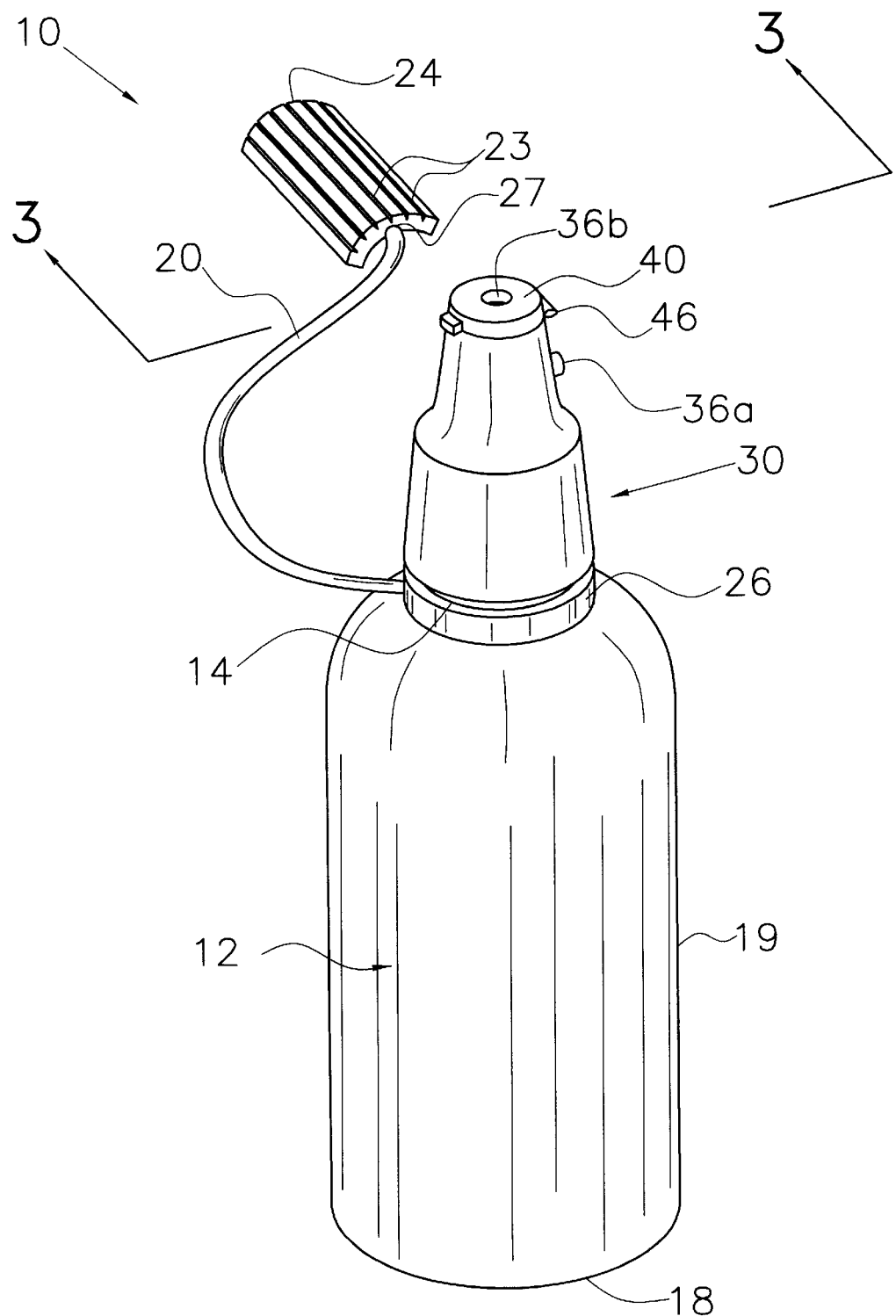
FIG. 2 is a perspective view of an eye drop applicator in accordance with the present invention, with the cover over the port in the cap so as to preserve sterility of the liquid medicament.
Figure 3:
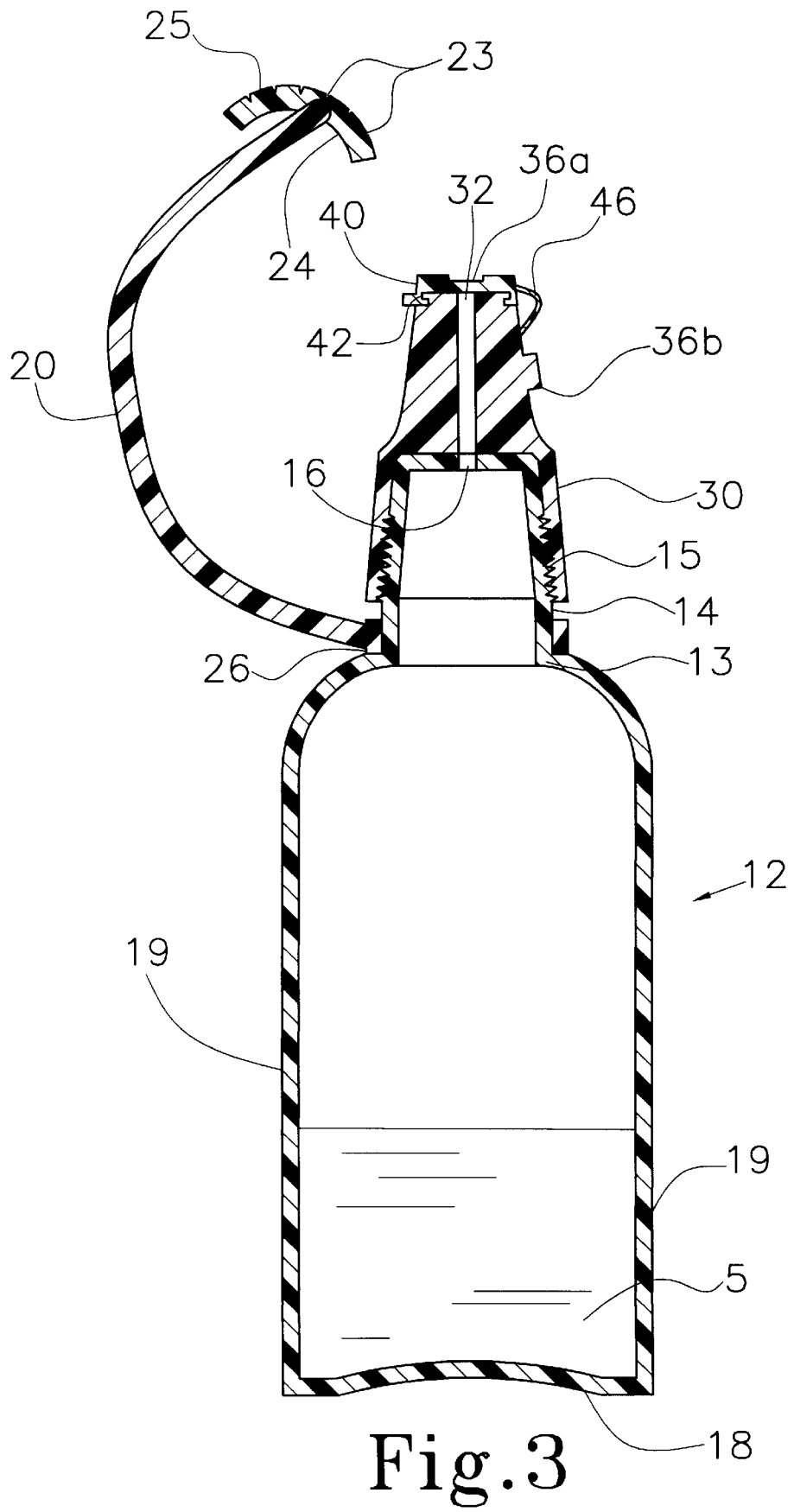
FIG. 3 presents a side view of the eye drop applicator of the present invention, in cross section, with the cover of the cap in its closed position.
Figure 4:
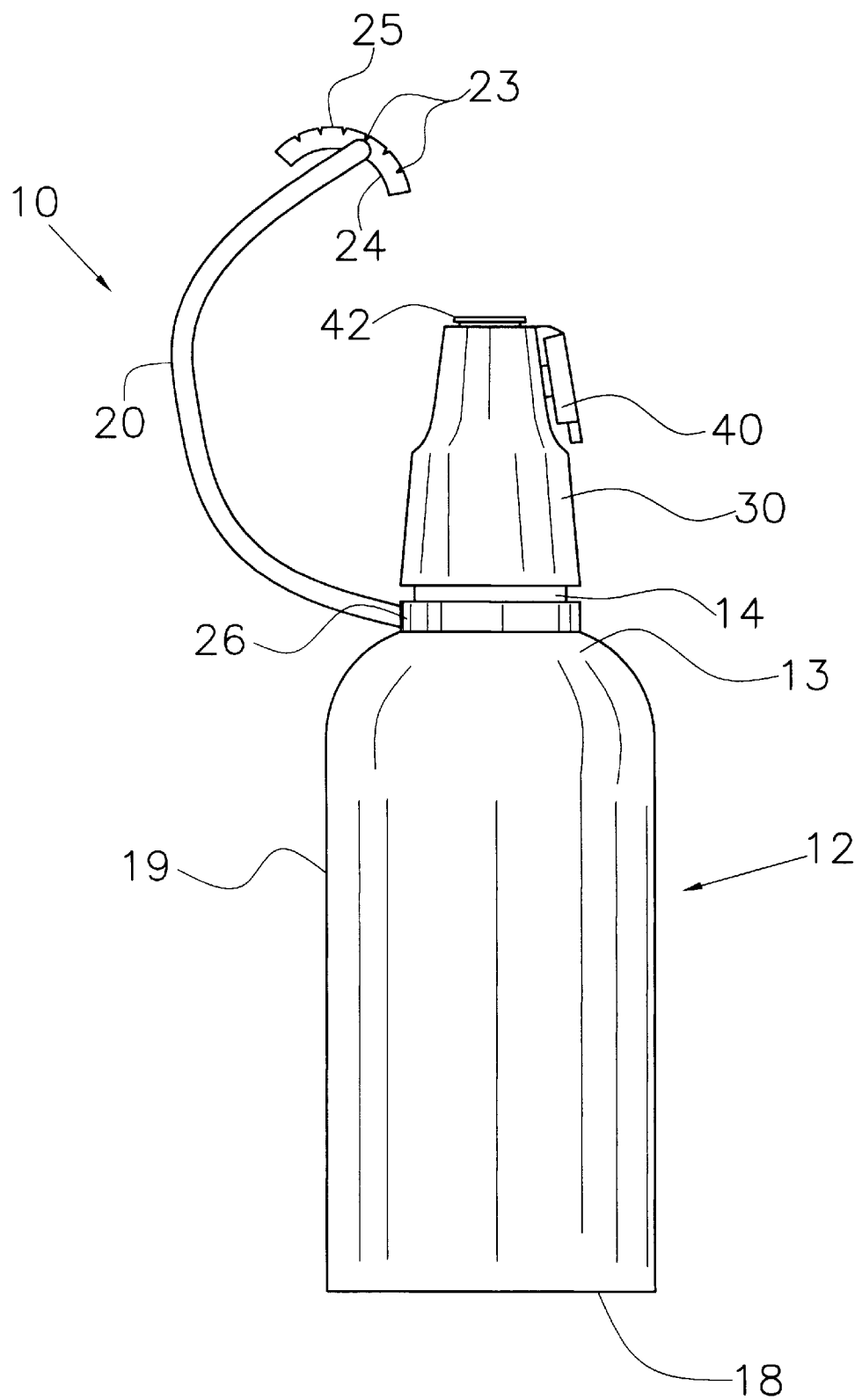
FIG. 4 is a side elevation view of the eye drop applicator showing the cover removed from the port in the cap.

A preferred embodiment of the apparatus of the present invention is shown generally at 10 in the perspective view of FIG. 1. FIG. 1 presents an eye drop applicator consisting first of a container 12 for holding liquid medicament. The container 12 may be of any size or shape that allows it to be held between the fingers of the user and positioned over the eye for dispensing liquid. In the preferred embodiment, the container 12 is a cylindrical bottle having a base 18. The base 18 allows the container 12 to rest upon a flat surface such as the shelf of a medicine cabinet.

The container 12 is fabricated from a light, pliable, and compressible material. An acceptable material, such as plastic, allows the user to squeeze liquid from the container by the exertion of gentle external force upon the sides 19 of the container 12. The aid of gravity is also invoked in that tilting the container to administer eye drops causes drops to fall from the pliable container and into the eye.

At the top of the container 12 and opposite the base 18 is a nozzle 14. The nozzle 14 extends from the cylindrical portion of the container 12, and allows liquid to be directed therefrom. The liquid medicament 5 exits the container from through opening 16 at the end of the nozzle 14.

The eye drop applicator of the present invention also includes a guide arm 20. The guide arm 20 is fabricated from a semi-rigid material. This allows the user to manipulate the shape of the guide arm 20 in order to properly position the container relative to the user's eye 2. The material must be flexible enough to allow manipulation so as to adjust the shape of the guide arm, but rigid enough to cause retraction of the lower eyelid when the container is rotated into place over the user's eye.

The guide arm 20 is fixedly attached to the container 12 at one end. In the preferred embodiment, attachment is accomplished by means of a ring 26 which is mounted over the nozzle 14. The ring 26 is attached to the guide arm 20 and is dimensioned to frictionally fit over the nozzle 14 at its base 13. It is further held in place by cap 30, which fits over the nozzle 14. Those skilled in the art will understand that attachment of the guide arm 20 may be accomplished in other ways, such as by directly fabricating the guide arm 20 into the container 12, or by fabricating the guide arm 20 into a cap 30 which is dimensioned to cover nozzle 14, as shown in an alternate embodiment per FIG. 6.

At the end of the guide arm 20 opposite the container 12 is a pad 24. The pad 24 serves as a point of tactile reference between the guide arm 20 and the cheek 6 of the user. In the preferred embodiment, the pad 24 is an arcuate roller attached to the guide arm 20. Relative to the cheek 6 of the user, the tactile surface 25 of the pad 24 is convex. This allows the guide arm 20 to remain in contact with the cheek 6 of the user as the container 12 is rotated upwards for administration of eye drops 5. This, in turn, allows the port 16 through which eye drops travel from the container 12 to remain at a fixed and proper distance from the eye 2.

In one embodiment, the guide arm 20 is fixedly attached to the pad 24 opposite the tactile surface 25. However, in the preferred embodiment, the guide arm 20 is received by a port 27 in a side of the pad 24. The port 27 is configured to allow the guide arm 20 to frictionally rotate about the axis of the guide arm 20.

To further facilitate the accurate administration of eye drops 5, the present invention provide for grooves 23 within the tactile surface 25 of the pad 20. The grooves 23 provide friction between the tactile surface 25 and the cheek 6 of the user. In this manner, greater control over the position of the container 12 is maintained by the user. Further, the grooves 23 assist the guide arm 20 in retracting the lower eyelid so as to expose the conjunctiva.

The eye drop applicator of the present invention 10 also provides a cap 30. The cap 30 is dimensioned to sealingly cover the nozzle 14 of the container 12, including through opening 16. In the preferred embodiment, the cap 30 is conical in shape, and is fastened to the nozzle 14 by means of a threaded connection 15. The cap 30 serves to maintain sterility of the through opening 16 in the nozzle 14, as well as the eye drops 5 within the container 12.

Provided at the top end of the cap 30 is a cap port 32. The cap port 32 is dimensioned to be of essentially the same dimensions as the nozzle through opening 16, and to be radially aligned with the nozzle port 16 when the cap 30 is over the nozzle 14. The cap port 32 provides a through opening which allows eye drops 5 to be dispensed from the container 12 without removal of the cap 30 itself.

To further insure sterility of the eye drops 5, a cap cover 40 is provided over the cap 30. The cover 40 defines a plastic or other semi-rigid and water proof material having an inwardly flanged shoulder 44. The cap cover 40 is configured to snap over and around a lip 42 extending up from the cap 30. In the preferred embodiment, the lip 42 is actually molded into the cap 30. The configuration of the shoulder 44 and lip 42 allow the cap cover 40 to be removable in such a manner that placement of the cover 40 over the cap 30 seals the eye drops 5 within the container 12, while removal of the cover 30 exposes the cap port 32 thereby allowing eye drops 5 to be dispensed from the container 12.

A danger of contamination to the cap cover 40 is presented when the cover 40 is removed from the cap 30. To avoid this risk, it is desirable to tether the cover 40 to the cap 30 itself. This not only facilitates ease to the user in locating the cover 40 after eye drops 5 have been dispensed, but also prevents the cover 40 from coming into contact with non-sterile surfaces. In the preferred embodiment, a tether 46 defining a semi-rigid strip of plastic is used to connect the cap 30 to the cover 40. Tethering in this manner allows for quick retrieval and placement of the cover 40 so as to preserve sterility of the eye drops 5.

Figure 7:
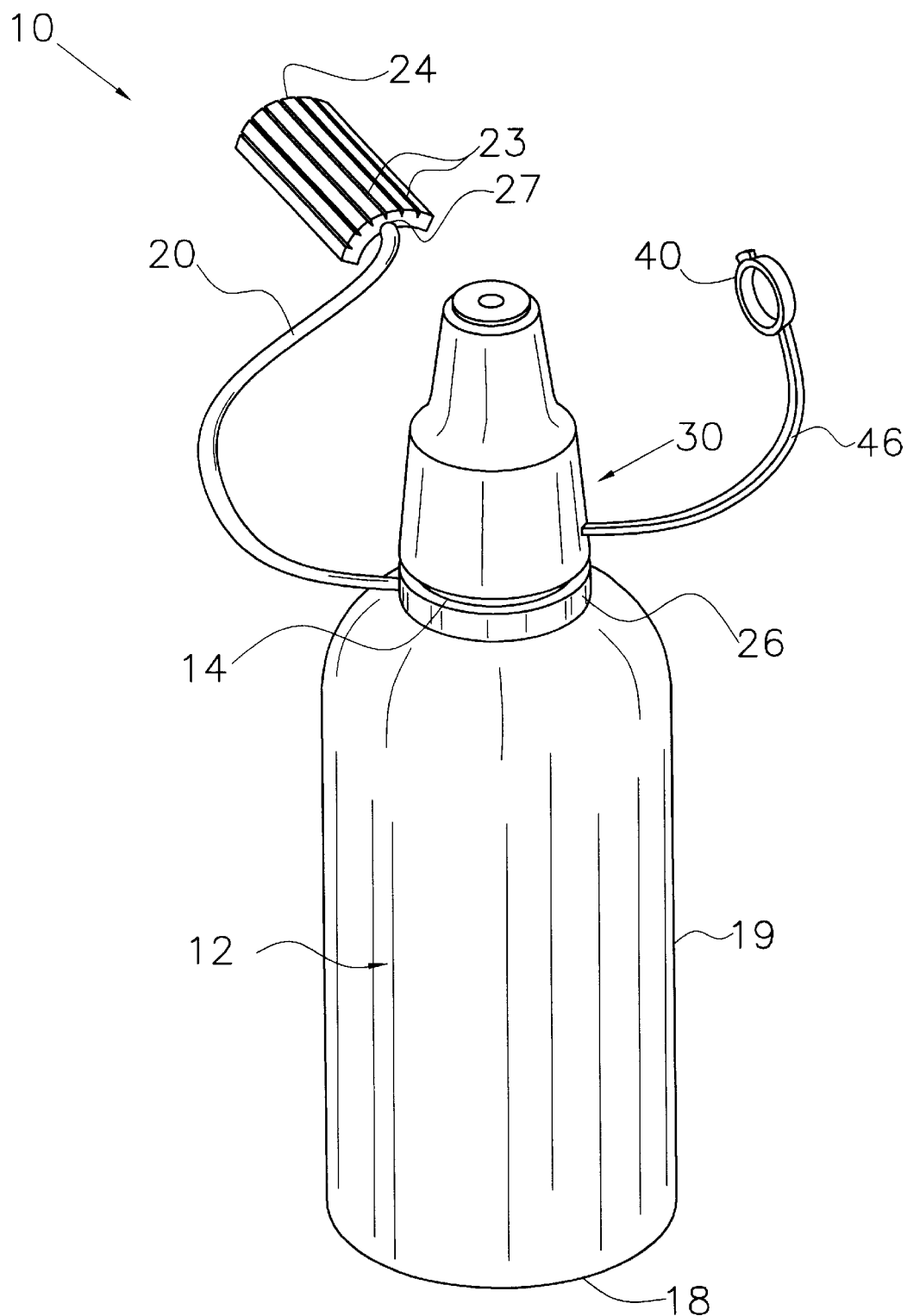
FIG. 7 presents a perspective view of the eye drop applicator of the present invention, with the cover tethered to the cap in an alternate manner.

Those skilled in the art will recognize that the use of a tether 46 creates the potential for interference when eye drops 5 are being dispensed. This is because inversion of the container 12 during the medication process creates a risk that the cover 40 may fall into the path in which the eye drops 5 are traveling. To avoid this potential, one embodiment of the present invention, shown in FIG. 7, provides a semi-rigid tether 46 affixed to the cap 30 near the base of the cap 30. Removal of the semi-rigid tether 46 from the cap port 32 allows eye drops to be dispensed without interference from the cover 40.

The preferred embodiment of the present invention maintains the unhindered flow of liquid medicament from the container 12 by providing a mortise and tenon fit for holding the cover 40 away from cap port 32. A mortise 36a is placed on the upper surface of the cover 40, which is configured to closely receive a tenon 36b within the side of the cap 30 itself. In the preferred embodiment, the mortise 36a and the tenon 36b are circular, and are configured to cause a friction fit which holds the cover 40 to the side of the cap 30. The mortise 36a and tenon 36b are fabricated into the cover 40 and cap 30, respectively. In this manner, the cover 40 is secured to the side of the cap 30 while medicament is being dispensed from the container 12. This again allows the unhindered the flow of eye drops 5 from the container into the eye 2.

The description given above presents an improved apparatus for dispensing eye drops. It will be appreciated that the guide arm within this invention enables the eye drop applicator to be safely and accurately used by any mature individual, regardless of the size or shape of their face. Moreover, the closure system enables the user to dispense eye drops without compromising sterility within the container. While a preferred embodiment for the foregoing has been shown and described, it will be understood that the description is not intended to limit the disclosures, but rather is intended to cover all modifications and alternate methods falling within the spirit and the scope of the invention as defined in the appended claims.

Figure 5:
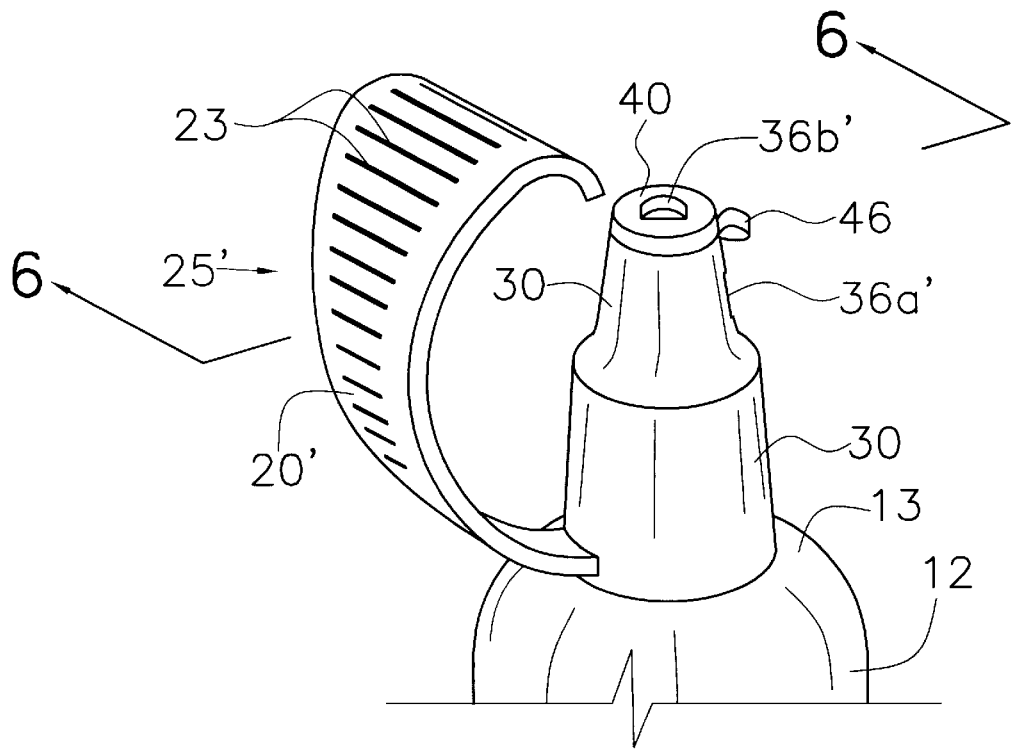
FIG. 5 depicts a perspective view of the eye drop applicator of the present invention, using an alternate embodiment of the guide arm.
Figure 6:
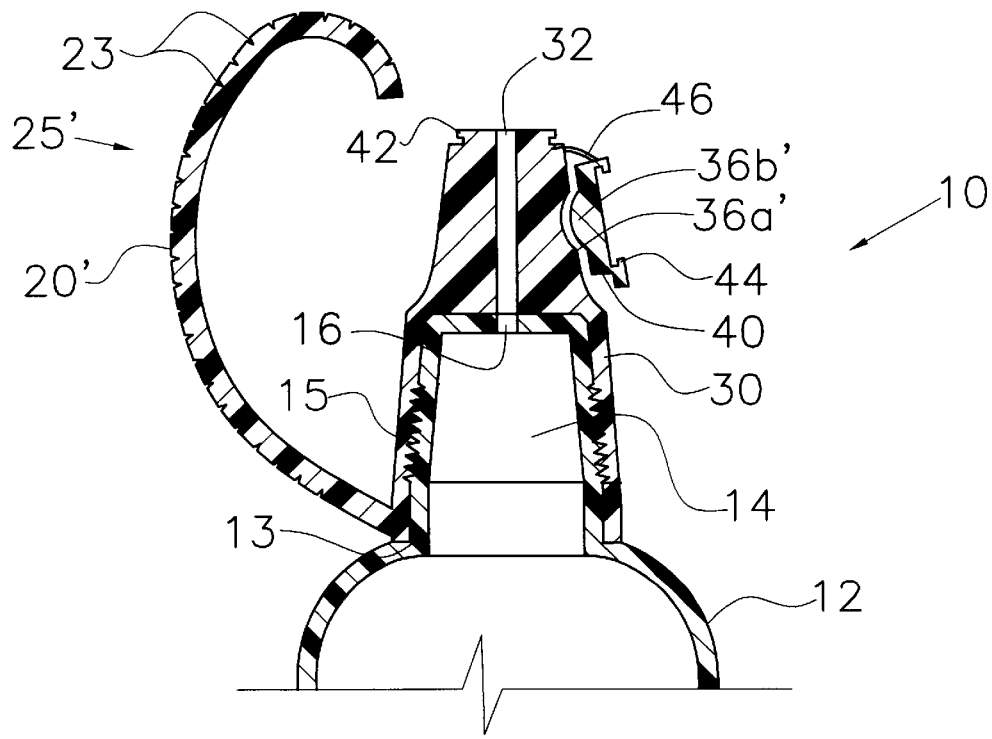
FIG. 6 illustrates the embodiment of the eye drop applicator of FIG. 5, in cross-section taken along 6—6 of FIG. 5.

An example of one such alternate embodiment is presented in FIG. 5 and FIG. 6. In this alternate embodiment, the guide arm 20 does not employ an attached pad 24 as the point of tactile reference for the user; rather, the guide arm 20 itself is configured to serve as the pont of tactile reference. To this end, the guide arm 20 defines an arcuate roller which, relative to the cheek 6 of the user, is convex. This allows the guide arm 20 to remain in contact with the cheek 6 of the user as the container 12 is tilted upwards for administration of eye drops 5. This, in turn, allows the port 16 through which eye drops travel from the container 12 to remain at a fixed and proper distance from the eye 2.

As with the primary embodiment in FIG. 1, the guide arm 20' in the alternate embodiment is fabricated from a semi-rigid material. This allows the configuration of the guide arm 20' to be adjusted in order to fit the face of the user. Also, the tactile surface 25' of the guide arm 20' presents grooves 23' which provide a frictional aid in retracting the lower eye lid of the user.

FIG. 5 and FIG. 6 also present an alternate embodiment for the mortise 36a and tenon 36b combination. In the alternate embodiment, the mortise 36a' is fabricated into the cap 30, while the tenon 36b' is fabricated into the cap cover 40. Those skilled in the art will recognize that other means for connecting the cap 30 and the cap cover 40 exist, and that the position and shape of such means may vary.

While the foregoing discussion has been directed to a complete applicator bottle, it will be apparent to those skilled in the art that novel features of the present invention reside in the guide arm and the closure system, and that these features could be advantageously placed onto a conventional eye drop bottle. This, of course, is provided that a compatible coupling means is included. Thus, a further aspect of the invention is a coupling means for connecting the guide arm and closure system of the present invention to a conventional eye drop bottle. Suitable means for coupling will depend on the nature of the bottle, but will generally be a threaded channel compatible with the threads of the bottle.

From the foregoing description, it will be recognized by those skilled in the art that an apparatus for dispensing liquid eye medicament offering advantages over previously known eye drop applicators has been offered. In particular, the present invention presents an adjustable guide arm attached to an eye drop container which provides for the proper positioning of the container relative to the conjunctiva. The applicator of the present invention can be used with one hand. In addition, the guide arm allows the user to position the container by means of tactile feedback. The user is not required to place his or her hands near the eye, thereby avoiding the risk that the eye drops become contaminated.

A further advantage of the invention is the closure system. The applicator provides a cap having a removable cover, which is tethered to the cap itself. In this way, eye drops can be dispensed from the applicator without necessity of removing the cap and setting it upon an unclean surface. However, the cap and cover can be removed from the container for cleaning.

Having thus described the aforementioned invention, I claim:

1. An eye drop applicator comprising:
    a bottle for holding liquid eye drops, said bottle having an upper portion and a lower portion, said upper portion defining a nozzle having a through opening, and said lower portion defining a compressible, hollow housing for the eye drops, said lower portion being movable between a first uncompressed position and a second compressed position;
    a removable cap coupled to said bottle, said cap configured to receive said nozzle, said cap also having a through opening which is aligned with said through opening of said nozzle;
    a detachable semi-rigid cover configured to seal said through opening in said removable cap; and
    a guide arm affixed to said eye drop applicator to retract the lower eye lid of the user, said guide arm comprising a first end and a second end, said first end being coupled to said bottle, and said second end being coupled to a pad which is placed under the eye of the user for retracting the lower eye lid, said guide arm being comprised of a semi-rigid material such that the disposition of said guide arm relative to said through opening in said cap is adjustable according to the shape of the face of the user.

2. An eye drop applicator according to claim 1 wherein said pad of said guide arm includes a connecting surface connected to said second end of said guide arm, and a tactile surface for making tactile contact with the user, and wherein said tactile surface defines at least one groove to assist in the retraction of the lower eye lid of the user.

3. An eye drop applicator according to claim 2 wherein said tactile surface is convex relative to the user.

4. The eye drop applicator according to claim 1, wherein said detachable cover is tethered to said cap.

* * * * *